(12) United States Patent
Kang et al.

(10) Patent No.: US 7,491,673 B2
(45) Date of Patent: Feb. 17, 2009

(54) METHOD FOR PREPARING A CATALYST FOR PARTIAL OXIDATION OF ACROLEIN

(75) Inventors: Jung Hwa Kang, Seoul (KR); Won Ho Lee, Daejun (KR); Min Ho Kil, Pusan (KR); Hyun Jong Shin, Chulranam-Do (KR); Byung Yul Choi, Seoul (KR); Yeon Shick Yoo, Chulranam-Do (KR); Young Hyun Choi, Chulranam-Do (KR); Ju Yeon Park, Chulranam-Do (KR)

(73) Assignee: LG Chem, Ltd., Seoul (KR)

( * ) Notice: Subject to any disclaimer, the term of this patent is extended or adjusted under 35 U.S.C. 154(b) by 925 days.

(21) Appl. No.: 10/498,901

(22) PCT Filed: Jul. 11, 2003

(86) PCT No.: PCT/KR03/01382

§ 371 (c)(1),
(2), (4) Date: Jun. 16, 2004

(87) PCT Pub. No.: WO2004/007071

PCT Pub. Date: Jan. 22, 2004

(65) Prior Publication Data

US 2005/0070736 A1    Mar. 31, 2005

(30) Foreign Application Priority Data

Jul. 12, 2002    (KR) ...................... 10-2002-0040642

(51) Int. Cl.
| | | |
|---|---|---|
| B01J 23/02 | (2006.01) |
| B01J 23/22 | (2006.01) |
| B01J 23/26 | (2006.01) |
| B01J 23/28 | (2006.01) |
| B01J 23/30 | (2006.01) |
| B01J 23/31 | (2006.01) |
| B01J 23/847 | (2006.01) |
| B01J 23/86 | (2006.01) |
| B01J 23/88 | (2006.01) |
| B01J 23/881 | (2006.01) |
| B01J 23/885 | (2006.01) |
| B01J 23/888 | (2006.01) |
| B01J 37/03 | (2006.01) |

(52) U.S. Cl. .................. 502/312; 502/311; 502/305; 502/306; 502/313; 502/316; 502/319; 502/321; 502/325; 502/328; 502/338; 502/340; 502/353

(58) Field of Classification Search ......... 502/311–313, 502/305, 306, 316, 319, 321, 325, 328, 338, 502/340, 353
See application file for complete search history.

(56) References Cited

U.S. PATENT DOCUMENTS

| | | | |
|---|---|---|---|
| 3,773,828 A | | 11/1973 | Kadowaki et al. |
| 4,259,211 A | * | 3/1981 | Krabetz et al. ............... 502/178 |
| 4,356,114 A | * | 10/1982 | Kadowaki et al. ........... 502/311 |
| 4,382,880 A | | 5/1983 | Derrien |
| 4,405,498 A | * | 9/1983 | Ebner ......................... 502/170 |
| 4,563,440 A | | 1/1986 | Forzatti et al. |
| 4,620,035 A | * | 10/1986 | Krabetz et al. ............... 562/534 |
| 4,892,856 A | | 1/1990 | Kawajiri et al. |
| 5,446,004 A | | 8/1995 | Tenten et al. |
| 6,171,998 B1 | | 1/2001 | Lee et al. |
| 6,383,978 B1 | * | 5/2002 | Bogan, Jr. ................... 502/311 |
| 6,384,275 B2 | | 5/2002 | Lee et al. |
| 7,078,563 B2 | * | 7/2006 | Ellis et al. ................. 560/241.1 |
| 7,285,514 B2 | * | 10/2007 | Kang et al. ................. 502/306 |

FOREIGN PATENT DOCUMENTS

| | | |
|---|---|---|
| JP | 49-169 A | 1/1974 |
| JP | 02-214543 A | 8/1990 |
| JP | 2001-038229 A | 2/2001 |
| JP | 2002-191974 A | 7/2002 |
| WO | WO-01/36364 A1 | 5/2001 |

* cited by examiner

*Primary Examiner*—Timothy C Vanoy
*Assistant Examiner*—Serena L Hanor
(74) *Attorney, Agent, or Firm*—Birch, Stewart, Kolasch & Birch, LLP

(57) ABSTRACT

The present invention provides a method for producing a catalyst comprising an inert carrier an a mixed metal oxide as a catalytically active component supported on the inert carrier, the method comprising the steps of: a) adding organic acid(s) into solvent(s) and salt of each metal component which will form a mixed metal oxide, to prepare a catalyst precursor solution for the mixed metal oxide; b) adjusting pH of the catalyst precursor solution using a basic solution; c) containing the catalyst precursor solution for the mixed metal oxide, of which the pH is adjusted, on the inert carrier, d) removing the solvent(s); and e) calcining the resultant from step d. The catalyst produced by the present method has improved reproducibility, activity and yield, while maintaining a high selectivity.

9 Claims, No Drawings

METHOD FOR PREPARING A CATALYST FOR PARTIAL OXIDATION OF ACROLEIN

TECHNICAL FIELD

The present invention relates to a catalyst for vapor phase partial oxidation comprising an inert carrier and a mixed metal oxide as a catalytically active component supported on the inert carrier; to a method for preparing the same; and to a method for preparing a partially oxidized organic compound by use of the catalyst.

BACKGROUND ART

A catalyst comprising a mixed metal oxide is useful for vapor phase partial oxidation of alkane, alkene or a mixture of alkane and alkene to an unsaturated carboxylic acid and for vapor phase oxidation of alkane, alkene or a mixture of alkane and alkene to unsaturated nitrile in the presence of ammonia.

For the production of acrylic acid, it has been widely practiced on a commercial scale a method which adopts acrolein as a raw material and affects the vapor phase partial oxidation thereof with molecular oxygen in the presence of a catalyst. Some patent applications disclosing a catalyst used for the production of the acrylic acid through the vapor phase oxidation of acrolein have been filed. The acrolein oxidation catalyst disclosed in the applications comprises molybdenum and vanadium as main components, and components, such as tungsten, chrome, copper, potassium and the like, are added, thereby improving capability thereof. For example, Japanese Patent Publication No. 12129/69 discloses a catalyst consisting of molybdenum, vanadium and tungsten, Japanese Patent Publication No. 25914/75 discloses a catalyst consisting of molybdenum, vanadium, copper and chrome, and Japanese Unexamined Patent Publication No. 85091/77 discloses a catalyst consisting of molybdenum, vanadium, copper, and at least one component selected from antimony and germanium. In addition, European Patent No. EP-023859 discloses that although the components and composition of the catalyst are identical, the conversion rate of the acrolein and a yield of the acrylic acid are significantly varied depending upon a method of forming the catalyst, when producing the catalyst. Also, the above European Patent discloses a method for producing the catalyst which produces acrylic acid at yields of high levels.

Recently, a demand for the catalyst having more high conversion rate and yield is increased. Studies for producing the corresponding catalyst are actively proceeding.

For example, when the catalyst for partially oxidizing the acrolein to the acrylic acid comprising the mixed metal oxide is prepared, it is difficult to uniformly maintain a suspension, since the precipitate is generated by reaction of a cationic metal salt with anionic metal salt in an aqueous solution, is rapidly settled when agitation is stopped and thus is phase separated from a water layer.

When containing on the inert carrier the suspension with the phase separation, it is difficult to maintain the uniformity, causing the uniformity problem of a catalyst article whenever the catalyst is produced. Also, if a particle size of a precipitate is large, it is difficult to transfer the suspension through a pumping operation and to contain the catalyst on the carrier using nozzle injection, so that the production thereof may run into a snag. In addition, the capacity of the catalyst is remarkably dependent upon the particle size of the metal salt contained in the suspension. Preferably, these metal salts consist of particles of less than 10 microns (refer to Korean Patent Publication No. 1998-073604). Accordingly, it is required to have a method of effectively suppressing the layer separation and decreasing the particle size of the suspension.

DISCLOSURE OF THE INVENTION

The present invention accomplishes the above demand by treating the precursor suspension for a mixed metal oxide with organic acid(s).

An object of the present invention is to provide a catalyst for vapor phase partial oxidation comprising an inert carrier and a mixed metal oxide as a catalytically active component supported on the inert carrier; to a method for preparing the same; and to a method for preparing a partially oxidized organic compound by use of said catalyst.

In order to accomplish the above mentioned objects, there is provided a method for producing a catalyst comprising an inert carrier and a mixed metal oxide as a catalytically active component supported on the inert carrier, the method comprising the steps of:

a) adding organic acid(s) into solvent(s) and salt of each metal component which will form said mixed metal oxide, to prepare a catalyst precursor solution for the mixed metal oxide;

b) adjusting pH of the catalyst precursor solution using a basic solution;

c) containing the catalyst precursor solution for the mixed metal oxide, of which the pH is adjusted, on the inert carrier;

d) removing the solvent(s); and e) calcining the resultant from step d.

According to another aspect of the present invention, there are provided a catalyst produced according to the above method; a method for producing an unsaturated carboxylic acid by vapor phase partial oxidation of alkane, alkene or a mixture of alkane and alkene in presence of said catalyst; and a method for producing an unsaturated nitrile by vapor phase partial oxidation of alkane, alkene or a mixture of alkane and alkene with ammonia in the presence of said catalyst.

The mixed metal oxide used as a catalytically active component in the catalyst for vapor phase partial oxidation is represented by the following formula 1, and said catalyst can be used for production of acrylic acid by oxidation of acrolein.

     Formula 1 wherein, Mo is molybdenum, W is tungsten, V is vanadium, O is oxygen, A is at least one element selected from a group consisting of iron, copper, bismuth, chrome, tin, antimony and potassium; and B is at least one element selected from a group consisting of alkali earth metals; a, b, c, d and e denote the atom ratio of the respective metals, respectively, provided that, in the case that a is 12, b is 1 to 5, c is 1 to 6, d is 1 to 5, e is 0 to 3, and x is a value determined depending upon oxidizing state(s) of other elements.

It is to be understood that both the foregoing general description and the following detailed description of the present invention are exemplary and explanatory and are intended to provide further explanation of the present invention as claimed.

BEST MODE FOR CARRYING OUT THE INVENTION

A method for producing a catalyst for partial oxidization comprising a mixed metal oxide will now be described in detail with reference to preferred embodiments of the present invention.

The present invention provides to the method for producing a catalyst for vapor phase partial oxidation comprising an inert carrier and a mixed metal oxide as a catalytically active component supported on the inert carrier, characterized by treating organic acid(s) when preparing a catalyst precursor suspension for the mixed metal oxides.

The organic acid is reacted with the metal salt, thereby producing a chelate compound. Since the produced chelate compound is easily soluble in water, precipitation of metal generated when producing metal oxide catalyst using a precipitating method may be prevented, and smaller catalyst particle may be produced. In addition, it is important to adjust the proper level of pH so as to improve the capability of the catalyst. In the case that the pH is not at the proper level, it was found that the capability of the catalyst is abruptly decreased.

The catalyst for vapor phase partial oxidation comprising the inert carrier and the mixed metal oxide as the catalytically active component supported on the inert carrier according to the present invention can be prepared in accordance with the method known in the art, except that the precursor solution treated by the organic acid is used. Specifically, the composition of catalyst, the method for production thereof, the kind of carrier, and the method for containing a catalyst component on the carrier may be each any of those known in the art.

The catalyst precursor solution for the mixed metal oxide as catalytically active component according to the present invention may be produced by mixing at least one solvent and metal salts in appropriate amounts to form the mixed metal oxide as catalytically active component, wherein the catalyst precursor solution may be a slurry, a dispersion, a solution or combination thereof. The solution is preferable. Solvent is then removed, and the precursor mixture is calcined.

An atomic ratio of the respective metal components in the solution, dispersion or slurry is previously determined to be a metal ratio of the mixed metal oxide catalyst component to be produced.

Suitable solvents for the precursor solution include water; alcohols including, but not limited to, methanol, ethanol, propanol, and diols, etc.; and other polar solvents known in the art. Generally, water is preferred. The water includes, without limitation, distilled water and deionized water. An amount of the water is preferably determined as an amount sufficient to keep the components substantially in solution enough to avoid or minimize compositional and/or phase separation during the production steps. Accordingly, the amount of water will vary depending upon the amounts and solubilities of the materials to be combined. Though lower amount of water are possible for forming the slurry, as described above, the amount of water is preferably sufficient to ensure that an aqueous solution is formed at the time of mixing.

In the method for producing the mixed metal oxide as catalytically active component, the metal compounds may be used in state(s) selected from ammonium salts, nitrates, various oxides, carbonates, chlorides, sulfates, hydroxides, organic acid salts, and the like.

In order to produce the chelate compound using the metal salt and the organic acid at the production of the precursor solution for the mixed metal oxide as catalytically active component, the amount of organic acid to be added should be adjusted, and the amount of added organic acid should be properly adjusted depending upon the total moles of molybdate of the metal salt.

To establish the effect of the acid-treatment, the amount of organic acid added in the production of the catalyst is in a mole ratio of 0.5 to 5, preferably 0.8 to 3.0, on the base of the molybdate. The pH of the precursor solution provided to maintain the capability of the catalyst is maintained in a range of 4 to 6 by use of base substance such as ammonia, pyridine, etc.

In the case of the precursor solution produced according to the present invention as described above, less than particle size of metal salt can be obtained, and the problem of phase separation of the precursor solution can be solved.

Preferably, the organic acid is a $C_1 \sim C_{10}$ organic acid comprising at least one of hydroxyl and carboxyl group. The organic acid usable in the present invention comprises citric acid, maleic acid, oxalic acid and the like, which is not limited thereto.

The inert carrier to be used in the present invention does not need to limit the material therefor.

The carrier, which can be used in producing the oxidizing catalyst for the production of the acrylic acid by the vapor phase partial oxidation of acrolein or an acrolein-containing gas, can use any of materials which are widely known as usable for the production. As examples of the material widely used for the carrier of the catalyst, it may be cited alumina, silica, silica-alumina, titania, magnesia, silica-magnesia, silica-magnesia-alumina, silicon carbide, silicon nitride, and zeolite, and preferably silica-alumina, silica-magnesia-alumina, silicon carbide or the like.

The carrier is not particularly limited on account of physical properties, shape, size etc. As respects the physical properties of the carrier, the specific surface area thereof is not more than $2 \, m^2/g$, preferably in the range of 0.01 to $1.5 \, m^2/g$, the water absorption ratio thereof is in the range of 0 to 70%, preferably 0 to 50%, and the average pore diameter thereof is in the range of 1 to 1,500 μm, preferably 5 to 500 μm. The shape of the carrier may be arbitrarily selected from sphere, cylinder, hollow cylinder and the like. The size is in the range of 1 to 10 mm, preferably 3 to 8 mm, in diameter in the case of spheres.

The amount of the catalytic component to be contained on the carrier is not particularly limited but is only required to be such that the produced catalyst permits effective production of acrylic acid by the vapor phase partial oxidation of acrolein. This amount, for example, is in the range of 1 to 200 wt. %, preferably 10 to 100 wt. %, based on the weight of the carrier for producing the acrylic acid.

The catalyst precursor solution treated by the organic acid according to the present invention is easily pumped and transferred, and can be injected through a nozzle, so that steps of containing the precursor solution for the mixed metal oxide on the inert carrier may be effectively performed. In addition, the present invention can solve the problem of the uniformity of article due to the layer separation, and a less than size of the metal salt can be obtained, thereby remarkably improving the capability of the catalyst.

Once the catalyst precursor solution treated by the organic acid according to the present invention is contained on the carrier, the liquid therein is removed by any suitable method known in the art. Such methods include vacuum drying, freeze drying, spray drying, rotary evaporation and air-drying, which it is not limited thereto. Vacuum drying is generally performed at pressure ranging from 10 mmHg to 500 mmHg. Freeze drying typically entails freezing the slurry, dispersion or solution, using, for instance, liquid nitrogen, and drying the frozen slurry, dispersion or solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mmHg to 760 mmHg, preferably at a bath temperature of from 40° C. to 90° C. and at a pressure of from 10 mmHg to 350 mmHg, more preferably at a bath temperature of from 40° C. to 60° C. and at a pressure of from 10 mmHg to 40 mmHg. Air drying may be effected at a temperature ranging from 25° C. to 90° C. The rotary evaporation or air-drying is generally preferred.

The catalyst precursor resulting from the drying is calcined. The calcination may be conducted in an oxygen-containing atmosphere or in an atmosphere free of oxygen (e.g., an inert atmosphere or vacuum). The inert atmosphere may be any material which is substantially inert, i.e., does not react or interact with the catalyst precursor. A suitable example includes, but it is not limited to, nitrogen, argon, xenon, helium or a mixture thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 $hr^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably for from 1 to 25 hours, more preferably for from 1 to 15 hours, to obtain the mixed metal oxide uniformly supported on the carrier.

As an example of the partially oxidized organic compound to be obtained by the use of the vapor phase partial oxidation catalyst according to the present invention, it may be cited an unsaturated aldehyde or an unsaturated carboxylic acid having not less than three carbon atoms and an organic acid anhydride or a nitrile compounds having not less than four carbon atoms. The unsaturated aldehyde or unsaturated carboxylic acid includes those having three to five carbon atoms, more preferably (meta)acrolein and (meta)acrylic acid. The organic acid anhydride or nitrile compound includes aromatic acid anhydride compounds, aromatic nitrile compounds and heterocyclic nitrile compounds, preferably organic acid anhydride, aromatic nitrile and heterocyclic nitrile having four to ten carbon atoms, and more preferably phthalic anhydride, maleic anhydride, pyromellitic anhydride, benzonitrile, picolino-nitrile and the like.

The method for producing the acrylic acid by the vapor phase partial oxidation of acrolein or an acrolein-containing gas in the presence of the catalyst according to the present invention has no particular restriction. It can be effected by any of the methods which can be used for reactions of this kind and which are widely known as usable therefor. The present invention can adopt any reaction conditions known to be available in producing acrylic acid at a fixed-bed multi-tube reactor. The production, for example, only requires acrolein or an acrolein-containing gas to contact with the catalyst at a temperature in the range of 180° C. to 350° C., preferably 200° C. to 330° C., under a normal pressure state or a pressurized state.

The present invention will now be described in detail with reference to the below embodiments and experiments. The embodiments are intended to be illustrative only, and the present invention is not limited thereto.

Production of Catalyst

EMBODIMENT 1

400 ml of distilled water was filled in a glass reactor having a volume of 500 cc and was agitated, while it was heated to a temperature of 97° C. 50 g of citric acid was solved thereto, and then 100 g of ammonium molybdate, 19.71 g of ammonium paratungsten and 22.09 g of ammonium metavanadate were solved. After the temperature of the resulting solution was lowered to 75° C., 21.67 g of copper nitrate and 6.29 g of strontium nitrate were inputted into the solution in turn to produce a suspension. The pH of the produced suspension was adjusted to 5.0 by use of an ammonium water.

The resulting suspension was contained on an inert carrier through a spray nozzle, and was coated on the carrier by drying it using a hot blast of 90° C. Such catalyst coated on the carrier was dried at a temperature of 120° C., and then was calcined at a temperature of 400° C. for 5 hours, with air flowing thereon, thereby producing the catalyst. At that time, the coated catalyst powders after the calcination were 25 wt %. The element composition of the produced catalyst components except for oxygen was $Mo_{12}W_{1.6}V_4Cu_{1.9}Sr_{0.63}$.

EMBODIMENT 2

A catalyst was produced in the same manner as used in Embodiment 1, except for that 100 g of citric acid is solved and the pH of the suspension is adjusted to 4.5 with ammonia water.

EMBODIMENT 3

A catalyst was produced in the same manner as used in Embodiment 1, except for that 100 g of citric acid is solved and the pH of the suspension is adjusted to 5.5 with ammonia water.

EMBODIMENT 4

A catalyst was produced in the same manner as used in Embodiment 1, except for that 60 g of oleic acid is solved instead of the citric acid.

EMBODIMENT 5

A catalyst was produced in the same manner as used in Embodiment 1, except for that 50 g of maleic acid is solved instead of the citric acid.

COMPARATIVE EMBODIMENT 400 ml of distilled water was filled in a glass reactor having a volume of 500 cc and was agitated, while it was heated to a temperature of 97° C. 100 g of ammonium molybdate, 19.71 g of ammonium paratungsten and 22.09 g of ammonium metavanadate were solved thereto. After the temperature of the resulting solution was lowered to 75° C., 21.67 g of copper nitrate and 6.29 g of strontium nitrate were inputted into the solution in turn to produce a suspension.

The resulting suspension was contained on an inert carrier through a spray nozzle, and was coated on the carrier by drying it using a hot blast of 90° C. Such catalyst coated on the carrier was dried at a temperature of 120° C., and then was calcined at a temperature of 400° C. for 5 hours, with air flowing thereon, thereby producing the catalyst. At that time, the coated catalyst powders after the calcination were 25 wt %. Element composition of the produced catalyst components excepting oxygen was $Mo_{12}W_{1.6}V_4Cu_{1.9}Sr_{0.63}$.

Example of Test

Catalyst Activating Test

The catalysts produced by the embodiments were filled in the reactor, and oxidation of acrolein was performed to produce acrylic acid. Reaction conditions for producing the acrylic acid are following: temperature of the reactor is 250° C. to 300° C.; pressure of the reactor is 1 to 3 atmospheric pressure; and raw gas of mixed gas, of which a volume ratio of acrolein:oxygen:vapor:nitrogen is 7.0:5.6:15:72.4, is introduced on the catalyst in 500 to 2000 hours of space velocity(STP). Results of the reaction tests on the embodiments and the comparative embodiment are shown in Table 1.

In the methods known in the art, as well as the conventional method described hereinbefore, it was reported that a conversion rate of the acrolein is more than 80%, a selectivity of the acrylic acid is 85% to 99%, and a yield of the acrylic acid is 77% to 98%. However, since conditions for testing the capability of the catalyst are various, it is insignificant to compare the above results with values disclosed in prior documents.

In the embodiments, the conversion rate of the acrolein and the yield of the acrylic acid are calculated according to the following Equations 1 and 2.

Conversion rate (%) of acrolein=[mole of reacted acrolein/mole of supplied acrolein]×100   Equation 1

Yield (%)=[mole of produced acrylic acid/mole of supplied acrolein]=100   Equation 2

TABLE 1

| Embodiment | Organic Acid | Catalyst Composition | Reacting Temp. (° C.) | Conversion Rate of Acrolein (%) | Yield of Acrylic Acid (%) |
|---|---|---|---|---|---|
| 1 | Citric Acid | $Mo_{12}W_{1.6}V_4Cu_{1.9}Sr_{0.63}$ | 270 | 99.32 | 89.75 |
| 2 | Citric Acid | $Mo_{12}W_{1.6}V_4Cu_{1.9}Sr_{0.63}$ | 270 | 99.21 | 89.55 |
| 3 | Citric Acid | $Mo_{12}W_{1.6}V_4Cu_{1.9}Sr_{0.63}$ | 270 | 99.12 | 89.35 |
| 4 | Maleic Acid | $Mo_{12}W_{1.6}V_4Cu_{1.9}Sr_{0.63}$ | 270 | 98.52 | 88.12 |
| 5 | Oleic Acid | $Mo_{12}W_{1.6}V_4Cu_{1.9}Sr_{0.63}$ | 270 | 98.10 | 87.43 |
| Comparative | — | $Mo_{12}W_{1.6}V_4Cu_{1.9}Sr_{0.63}$ | 270 | 95.21 | 84.23 |

While the present invention has been described and illustrated herein with reference to the preferred embodiments thereof, it will be apparent to those skilled in the art that various modifications and variations can be made therein without departing from the spirit and scope of the invention. Thus, it is intended that the present invention covers all modifications and variations of this invention that come within the scope of the appended claims and their equivalents.

INDUSTRIAL APPLICABILITY

On the base of the test results of acid treating the catalyst precursor solution using various organic acids in the production of catalyst, it can be appreciated that the present invention can provide a catalyst with improved reproducibility, activity and yield, while maintaining a high selectivity relative to the acrylic acid.

The invention claimed is:

1. A method for producing a catalyst comprising an inert carrier and a mixed metal oxide as a catalytically active component supported on the inert carrier, the method comprising the steps of:
   a) adding organic acid(s) into solvent(s) and salt of each metal component which will form a mixed metal oxide, to prepare a catalyst precursor solution for the mixed metal oxide;
   b) adjusting pH of the catalyst precursor solution in a range of 4 to 6 using a basic solution;
   c) containing the catalyst precursor solution for the mixed metal oxide, of which the pH is adjusted, on the inert carrier;
   d) removing the solvent(s); and
   e) calcining the resultant from step d,
   wherein the organic acid is added in a mole ratio of 0.5 to 5 on basis of molybdate.

2. The method as claimed in claim 1, wherein the mixed metal oxide used as a catalytically active component in the catalyst for vapor phase partial oxidation is represented by the following formula 1, and wherein the catalyst can be used for production of acrylic acid by oxidation of acrolein:

$$Mo_aW_bV_cA_dB_eO_x \qquad \text{Formula 1}$$

wherein, Mo is molybdenum, W is tungsten, V is vanadium, O is oxygen, A is at least one element selected from a group consisting of iron, copper, bismuth, chromium, tin, antimony and potassium, and B is at least one element selected from a group consisting of alkali earth metals; a, b, c, d and e denote atom ratio of the respective metals, respectively, provided that in case that a is 12, b is 1 to 5, c is 1 to 6, d is 1 to 5, e is 0 to 3, and x is a value determined depending upon oxidizing states of other elements.

3. The method as claimed in claim 1, wherein carbon atomicity of the organic acid is 1 to 10.

4. The method as claimed in claim 1, wherein the organic acid comprises at least one of hydroxyl and carboxyl group.

5. The method as claimed in claim 1, wherein the organic acid is selected from a group consisting of citric acid, maleic acid and oxalic acid.

6. The method as claimed in claim 1, wherein in the step b, the basic solution is ammonia or pyridine.

7. A catalyst for vapor phase partial oxidation comprising an inert carrier and a mixed metal oxide as a catalytically active component supported on the inert carrier, produced according to any one of claims 1, 2, 3, 4, 5 or 6.

8. A method for producing an unsaturated carboxylic acid by vapor phase partial oxidation of alkane, alkene or a mixture of alkane and alkene in the presence of the catalyst according to claim 7.

9. A method for producing an unsaturated nitrite by vapor phase oxidation of alkane, alkene or a mixture of alkane and alkene with ammonia in presence of the catalyst according to claim 7.

* * * * *